United States Patent [19]

Masao et al.

[11] Patent Number: 5,311,276

[45] Date of Patent: May 10, 1994

[54] APPARATUS FOR DETECTING CUT-EDGE FLAWS IN GLASS PLATES

[75] Inventors: Igisu Masao; Yoshiomi Toyota; Shoichi Kondo, all of Osaka; Masakazu Fujita, Tokyo; Hideo Kizuka, Tokyo; Kenkichi Sato, Tokyo, all of Japan

[73] Assignee: Nippon Sheet Glass Co., Ltd., Osaka, Japan

[21] Appl. No.: 397,424

[22] PCT Filed: Dec. 22, 1988

[86] PCT No.: PCT/JP88/01293

§ 371 Date: Aug. 11, 1989

§ 102(e) Date: Aug. 11, 1989

[87] PCT Pub. No.: WO89/06356

PCT Pub. Date: Jul. 13, 1989

[30] Foreign Application Priority Data

Dec. 25, 1987 [JP] Japan .................. 62-326697

[51] Int. Cl.$^5$ ............................................ G01N 21/89
[52] U.S. Cl. .................... 356/239; 356/237; 356/445
[58] Field of Search .................. 356/237, 239, 445

[56] References Cited

U.S. PATENT DOCUMENTS

3,359,853  12/1967  Benson et al. ................ 356/445

Primary Examiner—Vincent P. McGraw
Assistant Examiner—LaCharles P. Keesee
Attorney, Agent, or Firm—McGlew and Tuttle

[57] ABSTRACT

An apparatus for detecting flaws generated in the cut edges of cut glass plates is disclosed. The light emitted from a linear light source (11 and 21) and transmitted and reflected by a glass plate (1) is received by a one-dimensional imaging device (12 and 22), and the flaws in the cut edges of the glass plate are detected by a discriminator (13 and 24) based on the output voltage of the one-dimensional imaging device. The linear light source and the one-dimensional imaging device are disposed in such a manner that the longitudinal direction of the linear light source and the arranging direction of the imaging elements of the one-dimensional imaging device are parallel with each other, and that the longitudinal direction of the linear light source and the arranging direction of the imaging elements of the one-dimensional imaging device are oblique to the travelling direction of the glass plate on a plane parallel with the glass plate.

17 Claims, 6 Drawing Sheets

APPARATUS FOR DETECTING CUT-EDGE FLAWS IN GLASS PLATES

TECHNICAL FIELD

This invention relates to an apparatus for detecting flaws generated at the cut edges of glass plates.

BACKGROUND ART

The manufacture of glass plates generally involves the cutting and sorting of glass plates out of a glass strip pulled up from molten glass bath in the furnace as the glass strip travels on a line conveyor at a constant speed. In cutting the glass strip, trimming lines are marked in the direction parallel with the strip travelling direction by means of a trimming-line marker, cutting lines are marked in the direction perpendicular to the strip travelling direction by means of a diagonal cutter, and then the strip is cut along the cutting lines by means of a breaker and along the trimming lines by means of a slitter. In cutting the glass strip into a glass plate, various flaws are often caused on the cut edges of the glass plate, including chips produced by gouging the glass plate in a fish-scale shape in the through-thickness direction of the glass plate, serrations produced by gouging the glass plate in the through-thickness direction, burrs outwardly protruding from the cut line of the glass plate, and notches inwardly notched from the cut line of the glass plate.

Glass plates having such so-called cut-edge flaws have to be discarded as rejects. Conventional methods for detecting cut-edge flaws include the following.

First comes detection by visual inspection. This involves throwing a light beam from under a glass plate travelling on a line conveyor and monitoring by visual inspection the shadow of the glass plate projected on a screen located above the glass plate. With this method, such flaws as chips and serrations can be easily detected as shadows because light transmission remarkably deteriorated at chips and serrations, resulting in remarkably lowered transmitted light volume, while burrs and notches, which cause less changes in the volume of transmitted light, do not appear as clearly discernible shadows, making it difficult to detect them. In addition, visual inspection by human eyes has its limitation in terms of detecting accuracy.

Figure 1:
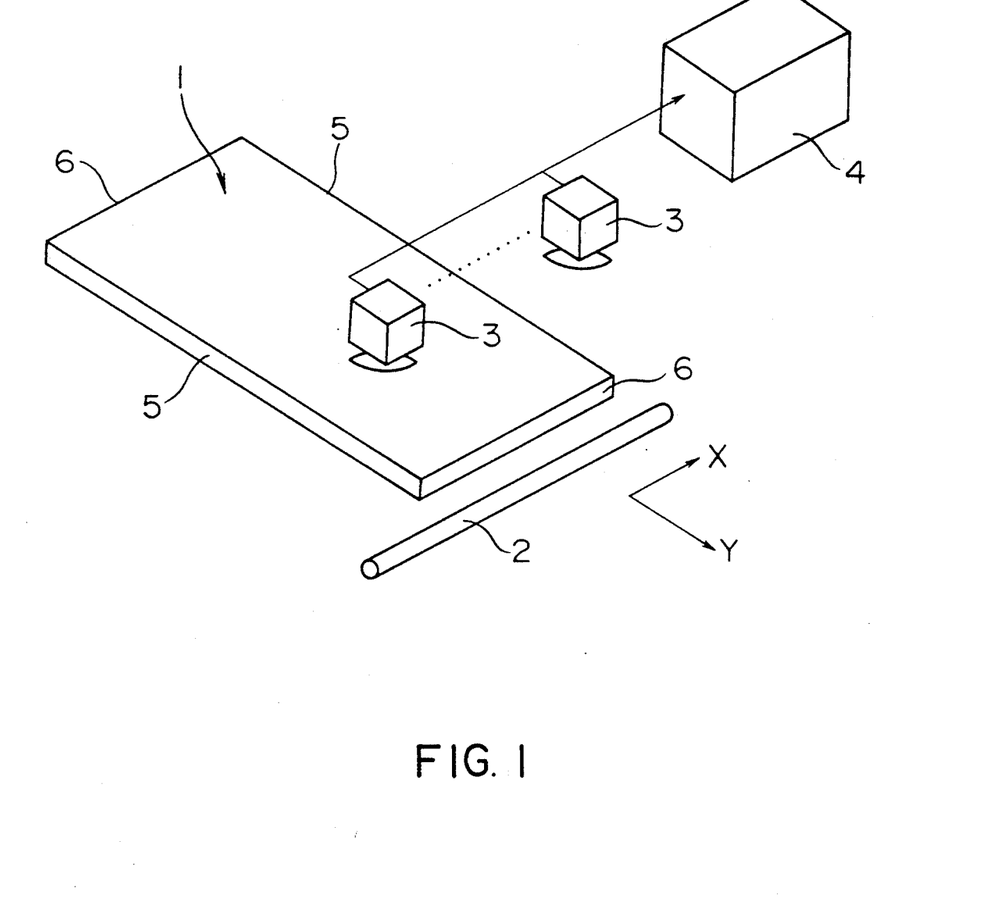
FIG. 1 is a drawing illustrating a cut-edge flaw detecting apparatus of the conventional type.

The prior art as shown in FIG. 1 is a cut-edge flaw detecting device which does not rely on visual inspection has such a construction that a fluorescent lamp 2 is disposed below a line conveyor carrying a glass plate 1. The fluorescent lamp 2 is positioned parallel with the plane of the glass plate 1 and perpendicular to the travelling direction of the glass plate 1, a plurality of 1024-bit one-dimensional CCD (charge-coupled device) camera 3 are disposed above the line conveyor to receive the light emitted from the fluorescent lamp 2 and transmitted through the glass plate 1. The outputs of the cameras 3 being sent to a discriminator 4 incorporating a microcomputer for processing to discriminate flaws present in the cut edges of the glass plate 1.

In the following description, the travelling direction of a glass plate on a plane parallel with the glass plate is termed as the Y-axis direction, and the direction orthogonal to the travelling direction of the glass plate as the X-axis direction.

Since the one-dimensional CCD cameras 3 of the conventional cut-edge flaw detecting apparatus are disposed in such a manner that the direction in which CCD-elements are arranged coincides with the X-axis direction, the apparatus can detect only cut-edge flaws present on the trimmer sides 5, i.e., two sides parallel with the Y-axis direction, but cannot detect those on the breaker sides 6, i.e., the two other sides parallel with the X-axis direction. Furthermore, this method, which also uses the CCD camera 3 to receive transmitted light has low accuracy in detecting burrs and notches for the same reasons as described above.

The conventional cut-edge flaw detecting device, which judges the size of a cut-edge flaw based on the magnitude of the differentiation signal obtained by differentiating the output of the CCD camera 3, has low accuracy in judging the size of flaw because the size of the cut-edge flaw is not necessarily proportional to the size of the differentiation signal.

DISCLOSURE OF INVENTION

It is an object of this invention to provide an apparatus for detecting cut-edge flaws that solves problems inherent in the prior art as described above, and is capable of detecting with high accuracy chips, serrations, burrs, notches and other flaws present in the cut edges on all four sides (trimmer and breaker sides) of a glass plate transported at high speed, and the size thereof.

It is another object of this invention to provide an apparatus for detecting cut-edge flaws that is suitable for detecting flaws which were formed by gouging the glass plate in the through-thickness direction, such as chips and serrations.

It is still another object of this invention to provide an apparatus for detecting cut-edge flaws that is suitable for detecting flaws which were protruded or notched from the cut line of the glass plate.

The apparatus for detecting cut-edge flaws in glass plates according to this invention has a linear light source disposed on a plane parallel with a glass plate being transported, and in an oblique direction with respect to the travelling direction of the glass plate, a one-dimensional imaging device whose imaging-elements are arranged in parallel with the above-mentioned linear light source, and a discriminator for discriminating the size of a flaw present in the cut edge of the glass plate based on the light detected by the above-mentioned one-dimensional imaging device.

Using the apparatus for detecting cut-edge flaws in glass plates of this invention, those cut-edge flaws which were formed by gouging the glass plate in the through-thickness direction can be detected by detecting changes in the volume of transmitted light since light transmission is deteriorated through such flaws.

Those cut-edge flaws which were protruded or notched from the cut line of glass plate can also be detected by using reflected light. That is, such a flaw can be detected by throwing light on a travelling glass plate, detecting the light reflected from the surface of the glass plate, obtaining the positional coordinates of four corner points of the glass plate using the image processing technology based on computer software, obtaining imaginary straight lines connecting these adjoining corner points, and discriminating those portions that shift from the imaginary lines as flaws and calculating the size thereof.

In order to allow the four sides of a glass plate to be detected, a linear light source and a one-dimensional imaging device are disposed in this invention in such a manner that the longitudinal direction of the linear light source and the arranging direction of imaging elements of the one-dimensional imaging device are disposed in parallel with each other and obliquely with respect to the glass-plate travelling (Y-axis) direction on a plane parallel with the glass plate. Particularly, when the linear light source and the one-dimensional imaging device are disposed at 45° with respect to the Y-axis direction, both the trimmer and breaker sides can be detected at the same resolution, making data processing in the discriminator easy.

The apparatus for detecting cut-edge flaws in glass plates of this invention is therefore capable of simultaneously detecting flaws present on the trimmer and breaker sides of a glass plate, and of accurately determining the size of chips, serrations and other cut-edge flaws which were formed by gouging the glass plate in the through-thickness direction as well as burrs, notches and other cut-edge flaws which were protruded or notched from the cut line of glass plate.

BEST MODE FOR CARRYING OUT THE INVENTION

In the following, an embodiment of the cut-edge flaw detecting apparatus of this invention will be described.

The cut-edge flaw detecting apparatus of this invention comprises a cut-edge flaw detector for detecting chips, serrations and other flaws which were formed by gouging the glass plate in the through-thickness direction by detecting transmitted light, and another cut-edge flaw detector for detecting burrs, notches and other flaws that were protruded or notched from the cut line of the glass plate by detecting reflected light.

Figure 2A:
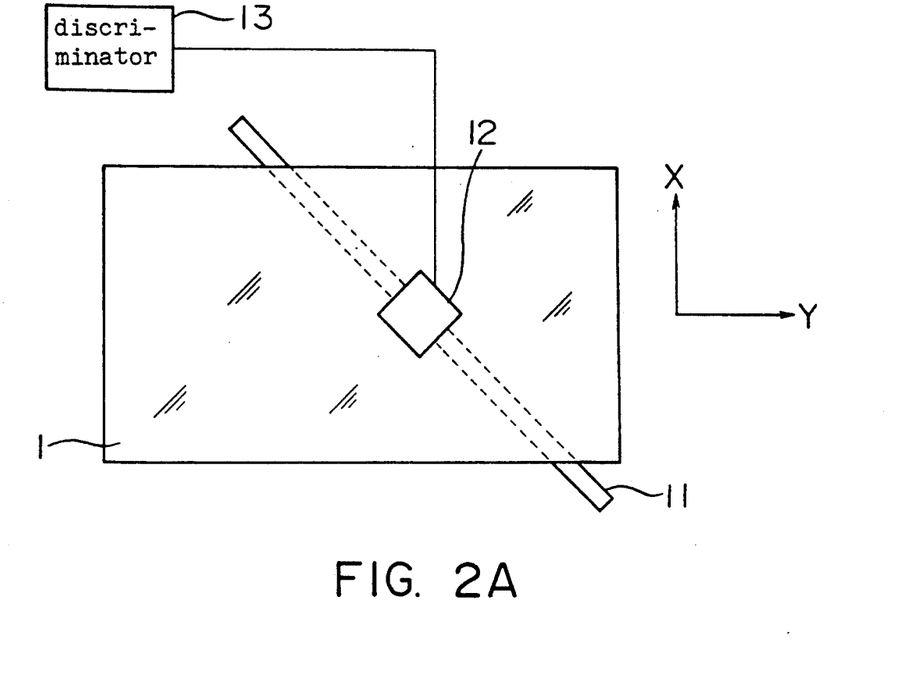
FIGS. 2A and 2B are diagrams illustrating a cut-edge flaw detector relying on transmitted light, used in the apparatus for detecting cut-edge flaws in glass plates of this invention.
Figure 2B:
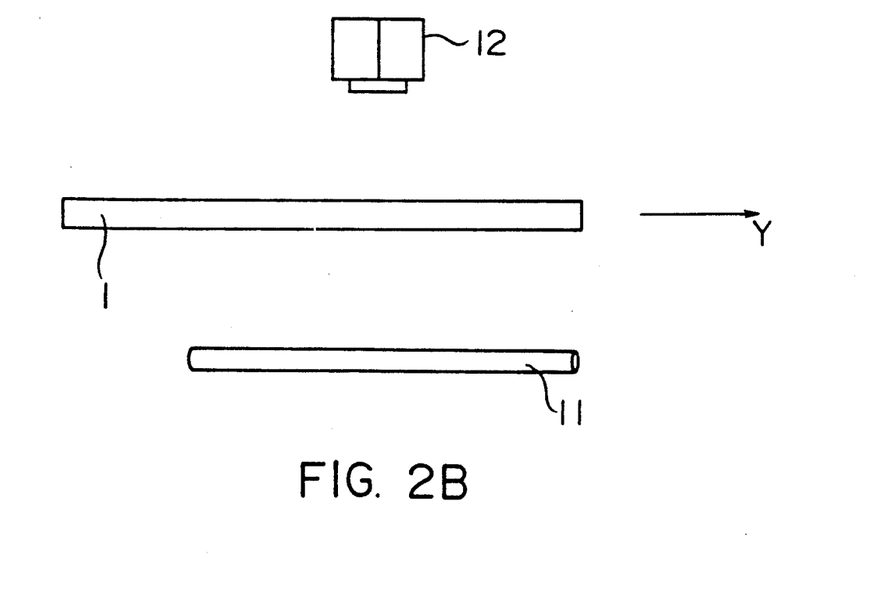
Figure 3:
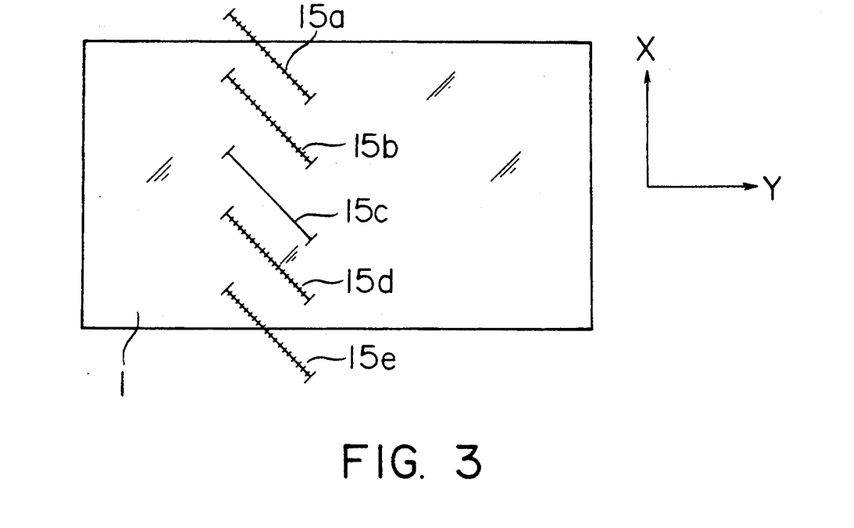
FIG. 3 is a diagram illustrating the field of each of a plurality of CCD cameras.

FIGS. 2A and 2B are a plan view and side elevation, respectively, of the cut-edge flaw detector relying on transmitted light. This cut-edge flaw detector comprises a fluorescent lamp 11 disposed below a glass plate 1, which is transported at a constant speed on a conveyor, in such a manner that the longitudinal direction thereof makes a 45° angle with respect to the Y-axis direction on a plane parallel with the glass plate 1. A plurality of one-dimensional CCD cameras 12 are disposed above the glass plate 1 in parallel with the fluorescent lamp 11 in such a manner that the arranging direction of the CCD elements thereof makes a 45° angle with respect to the Y-axis direction on a plane parallel with the glass plate 1. A discriminator 13 judges the acceptability of glass plates by processing the output waveforms from the CCD cameras 12 and comparing the size of the flaws with the reference values. In FIGS. 2A and 2B, only one unit of the one-dimensional CCD camera 12 is shown for simplicity. In practice, however, a plurality (5 units in FIG. 3) of CCD cameras are disposed in such a manner that the fields 15a, 15b, 15c, 15d and 15e thereof are overlapped to form a continuous field as a whole, as shown in FIG. 3. The advantages of the above-mentioned arrangement in which the one-dimensional CCD camera is disposed at a 45° angle with respect to the Y-axis direction on a plane parallel with the glass plate 1 are that flaws on all the four sides of the glass plate 1 can be detected, and that flaws on both the trimmer 5 and breaker 6 sides can be detected at the same resolution.

In this embodiment, a high-frequency or d-c fluorescent lamp is employed as the fluorescent lamp 11 to reduce flickering. As the one-dimensional CCD camera 12, a 2048-bit CCD camera is used. The 2048-bit CCD camera has a field of 400 mm, and therefore a resolution of approximately 0.2 mm segments.

Using the cut-edge flaw detector of the above-mentioned arrangement, the light from the fluorescent lamp 11 is transmitted through the glass plate 1 and received by the CCD camera 12. If a chip or a serrated flaw is present on the edge of the glass plate 1, the volume of the light transmitted through the flaw becomes smaller than that of the light transmitted through the glass-plate area free of flaws.

Figure 4:
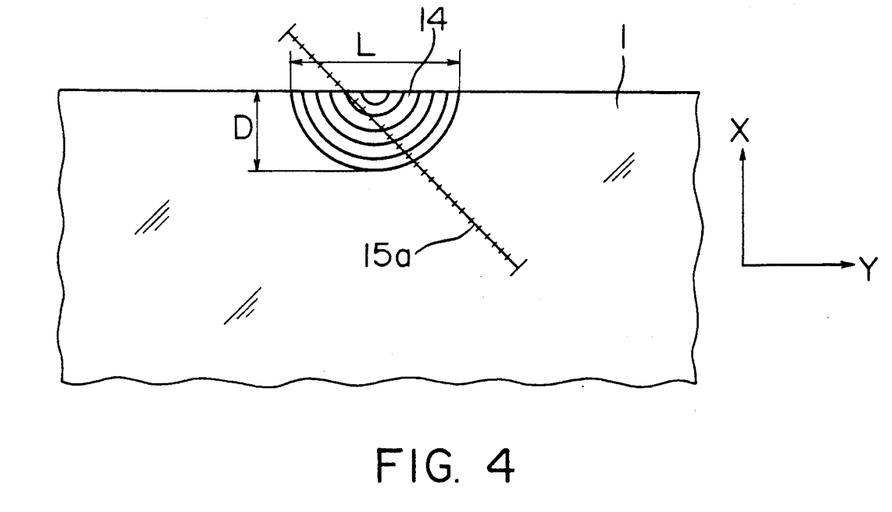
FIG. 4 is a diagram of assistance in explaining the detection of a chip.
Figure 5:
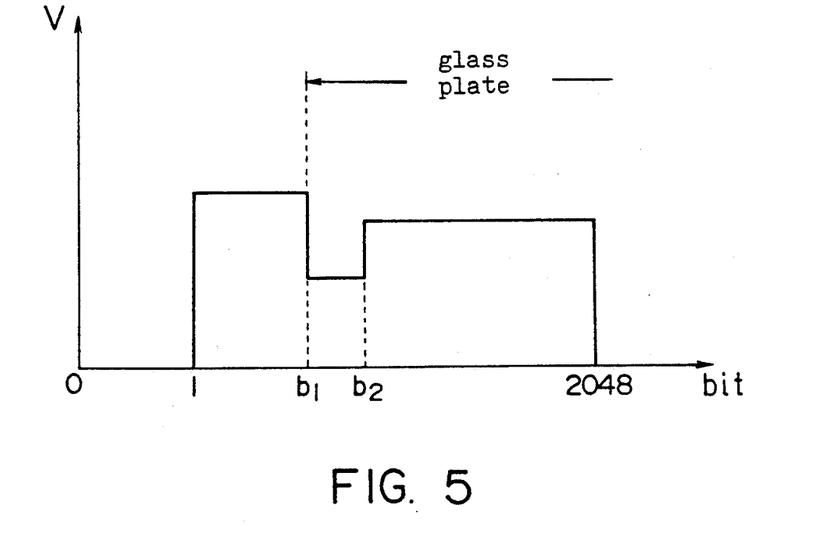
FIG. 5 is a diagram of the output waveform of the CCD camera.

Now, the output waveform for one scan of the CCD camera 12 when there is a chip 14 on the trimmer side of the glass plate 1, as shown in FIG. 4, will be described. FIG. 5 shows the output waveform of the CCD camera when the light transmitted through the chip 14 is received. The ordinate of the figure represents the output voltage V, and the abscissa the bits of CCD elements. The output voltage for $1-b_1$ bits is produced by the light coming from the outside of the glass plate, that is, by the light that is not transmitted through the glass plate, representing the largest output voltage. The output voltage for $b_1-b_2$ bits is produced by the light transmitted through the chip 14, falling to a lower level as the result of the reduced volume of transmitted light due to the flaw. The output voltage for $b_2-2048$ bits is generated by the light transmitted through the glass-plate area free of flaws. In this case where the volume of light is slightly reduced as it passes through the glass plate, the output voltage is slightly lower than that produced by the light not transmitted through the glass plate.

The discriminator 13 has a counter to count the number of bits at the fall region ($b_1-b_2$ bits in FIG. 5) of the output voltage fed by the CCD camera at each scan, and the number of continued scans in the fall region to discriminate the size of flaw. The size of flaw is evaluated by two parameters of the "length L" parallel with the side of the glass plate and the "width D" perpendicular to the side of the glass plate, as shown in FIG. 4. Since the one-dimensional CCD elements of the CCD camera are disposed at a 45° angle with respect to the Y-axis direction, the count value of the number of bits and the count value of the number of scans do not correspond on a one-to-one basis to the "length L" and "width D" of a flaw. These values are therefore multiplied by coefficients in the discriminator 13.

The above operation is carried out for the field covered by each CCD camera, and the output voltages from all the CCD cameras are fed to the discriminator 13. In the discriminator, flaw information for all the four sides of a glass plate can be obtained after the glass plate has passed through the flaw detector. If there is a flaw, therefore, the "length L" and the "width D" of the flaw are compared with the reference values stored in advance in the discriminator 13 to judge the acceptability of the glass plate.

Next, another cut-edge flaw detector, that is, the cut-edge flaw detector for detecting burrs, notches and other flaws will be described.

Figure 6A:
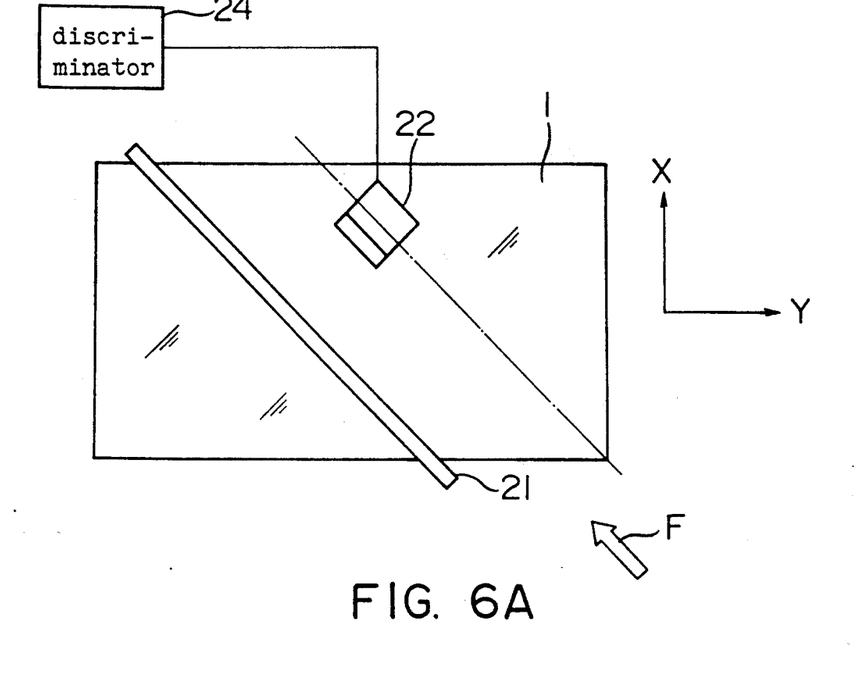
FIGS. 6A and 6B are diagrams illustrating a cut-edge flaw detector relying on reflected light, used in the apparatus for detecting cut-edge flaws in glass plates of this invention.
Figure 6B:
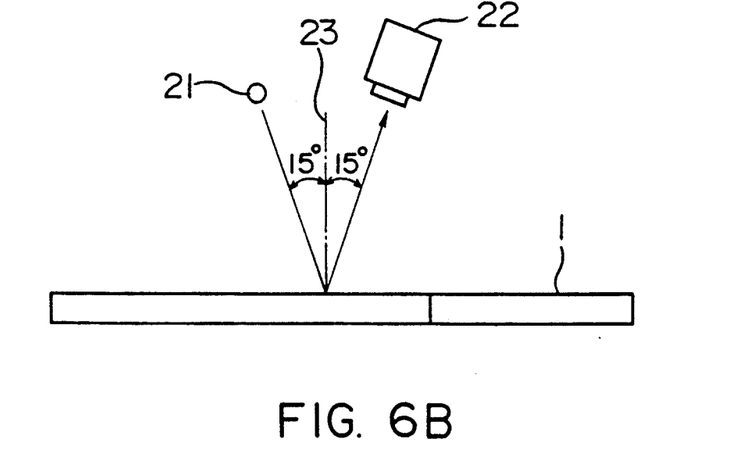

FIGS. 6A and 6B are a plan view of the cut-edge flaw detector, and a side elevation of the same, viewed from the direction inclined at 45° to the Y-axis direction, that is, the direction shown by an arrow F, respectively. This cut-edge flaw detector comprises a fluorescent lamp 21 disposed above a glass plate 1 that is transported at a constant speed on the line conveyor. The length of the fluorescent lamp 21 makes a 45° angle to the Y-axis direction on a plane parallel with the glass plate 1. A plurality of one-dimensional CCD cameras 22 disposed above the glass plate and in parallel with the fluorescent lamp 21 in such a manner that the arranging direction of the CCD elements makes a 45° angle to the Y-axis direction on a plane parallel with the glass plate 1. As shown in FIG. 6B which is a side elevation viewed from the direction shown by the arrow F in FIG. 6A, both the fluorescent lamp 21 and the CCD camera 22 are disposed at a 15° angle with respect to the normal line 23.

The fluorescent lamp 21 and the one-dimensional CCD camera 22 are of similar types to those used in the cut-edge flaw detector shown in FIGS. 2A and 2B. That is, the fluorescent lamp 21 is a high-frequency or d-c fluorescent lamp, and the one-dimensional CCD camera 22 is of a 2048-bit type having a field of 400 mm. Although only one unit of CCD camera is shown in FIGS. 6A and 6B, a plurality of CCD cameras are disposed in the actual embodiment.

This cut-edge flaw detector has a discriminator 24 which judges the acceptability of a glass plate by processing the output waveforms from the CCD cameras, discriminating the size of flaw, and comparing the flaw size with the reference values.

Figure 7:
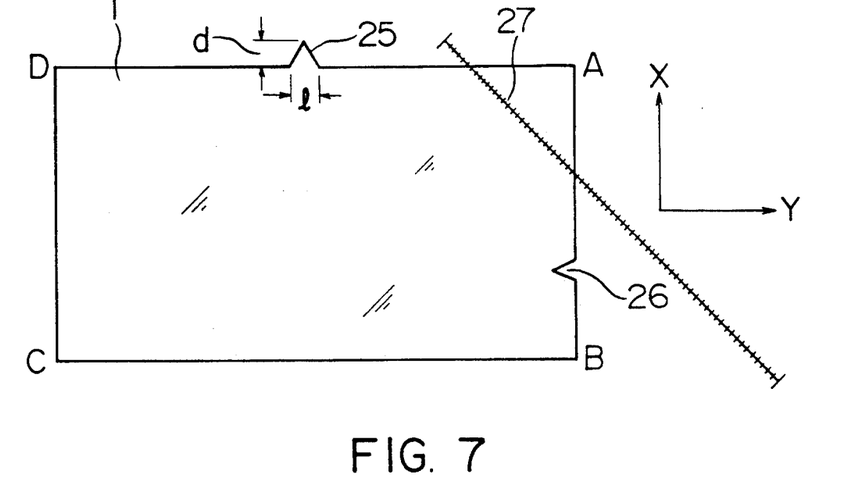
FIG. 7 is a diagram of assistance in explaining the detection of burrs and notches.

Using the cut-edge flaw detector of the above-mentioned arrangement, the light emitted from the fluorescent lamp 21 is reflected by the surface of the glass plate 1 and picked up by the CCD camera 22. As shown in FIG. 7, if there is a burr 25 on the trimmer side of the glass plate 1, and a notch 26 on the breaker side, the light thrown on the burr 25 is reflected and received by the CCD camera, while the light thrown on the notch 26 is not reflected and received by the CCD camera. In FIG. 7, reference numeral 27 refers to a field covered by a plurality of CCD cameras.

Figure 8:
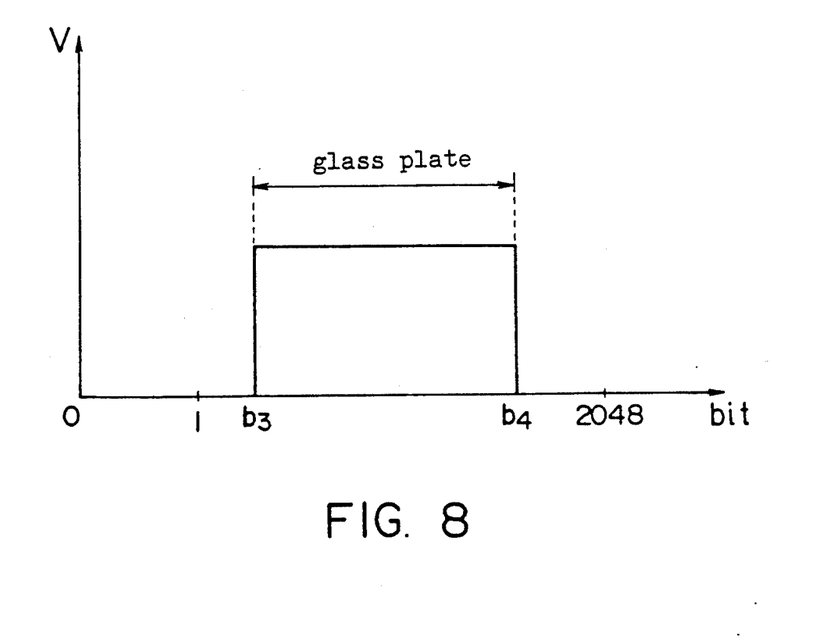
FIG. 8 is a diagram of the output waveform of the CCD camera.

The output waveform for one scan of the CCD cameras which took the image in the field 27 shown in FIG. 7 is shown in FIG. 8. The ordinate of the figure represents the output voltage V, and the abscissa the bit of the CCD elements. The waveform rises at $b_3$ bit and falls at $b_4$ bit. Consequently, the bit change points, that is, the points at which the waveform changes represent the edges, i.e., sides of the glass plate 1.

In the discriminator 24, the output voltages from all the CCD cameras are input, and coordinates are calculated by assuming the bit change points as the sides of the glass plate.

Figure 9:
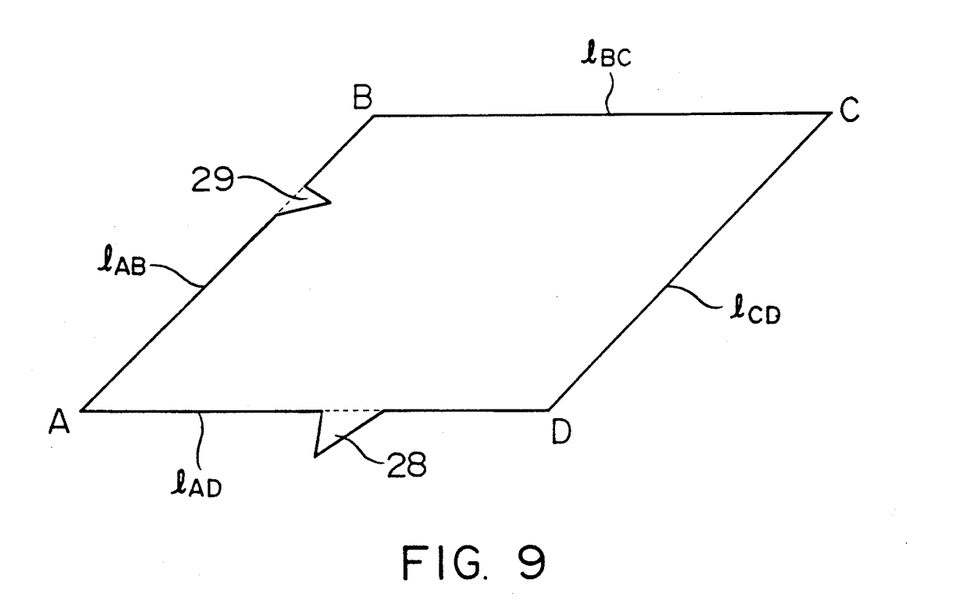
FIG. 9 is a diagram of assistance in explaining how to obtain imaginary straight-lines.

FIG. 9 shows the state of shift in the bit change points when the corners of the glass plate 1 are assumed to be A, B, C and D.

As the glass plate 1 travels at a constant speed in the Y-axis direction, the bit change points for the breaker sides AB and CD are shifted at a given rate, while the bit change points for the trimmer sides AD and BC are not shifted, remaining constant. In the discriminator 24, the points at which the bit change points are shifted from the shifting state to the steady state, or from the steady state to the shifting state are regarded as the corners A, B, C and D of the glass plate 1, and imaginary straight-lines $l_{AB}$, $l_{BC}$, $l_{CD}$ and $l_{AD}$ connecting these points are obtained. These imaginary straight-lines correspond to the sides of the glass plate free of flaws. Actually, the trimmer side AD has a burr 25 and the breaker side AB has a notch 26, as shown in FIG. 7. The state of shift in the bit change points shown in FIG. 9 therefore has portions 28 and 29 that deviate from the imaginary straight-lines.

In the discriminator 24, the difference between the coordinate data of the actually calculated bit change points and the imaginary straight-lines is obtained at each sampling point, and the size of the burr or notch is calculated from the difference obtained. The size of flaw is evaluated by the two parameters of the "length l" parallel with the sides of the glass plate and "width d" perpendicular to the sides. In the discriminator 24, the acceptability of glass plates is judged by comparing the "length l" and "width d" of the flaw with the reference values stored in advance in the discriminator 24.

Although an embodiment of this invention has been discussed in the foregoing, the linear light source may be a combination of a point light source and a parabolic mirror. Reflected light and transmitted light may be temporarily projected on a screen to pick up the projected image with CCD cameras, instead of picking up reflected light and transmitted light directly by CCD cameras.

The above embodiment comprises a cut-edge flaw detector for detecting chips, serrations and other flaws which were formed by gouging the glass plate in the through-thickness direction by detecting transmitted light, and a cut-edge flaw detector for detecting burrs, notches and other flaws which were protruded or notched from the cut lines by detecting reflected light. Needless to say, however, these cut-edge flaw detectors may be provided independently.

Industrial Applicability

Since the apparatus for detecting cut-edge flaws in glass plate of this invention can detect various types of flaws generated at the cut edges of a glass plate in the glass-plate cutting process, quality control can be effected by providing the apparatus in the glass-plate manufacturing line or the final product inspection line. The cut-edge flaw detector of this type can be used for detecting flaws in the cut edges of not only glass plate but also transparent sheeting.

We claim:

1. An apparatus for detecting cut-edge flaws in a travelling transparent plate comprising:
    a first linear light source disposed on one side of the travelling glass plate, arranged substantially parallel with the transparent plate and obliquely aligned with respect to the travelling direction of the transparent plate;

first one-dimensional imaging means disposed on a second side of the transparent plate and having imaging elements parallel with said first linear light source for detecting light emitted from said first linear light source and transmitted through the transparent plate;

a first discriminator means for identifying flaws and discriminating between flaws in dependance on flaw size in edges of the glass plate based on change in volume of said transmitted light detected by said first one-dimensional imaging means;

a second linear light source disposed on said first side of the travelling glass plate, arranged substantially parallel with the transparent plate and obliquely aligned with respect to the travelling direction of the transparent plate;

a second one-dimensional imaging means disposed on said first side of the transparent plate having imaging elements parallel with said linear light source for detecting light emitted from said linear light source and reflected by the surface of the transparent plate; and a second discriminator means for identifying flaws and discriminating between flaws in dependance on flaw size in the edges of the transparent plate and detecting the size of the flaw based on reflected light detected by said second one-dimensional imaging device.

2. An apparatus for detecting cut-edge flaws in transparent plates set forth in claim 1 wherein:
said first and second linear light source are formed of a fluorescent lamp; and
the first and second one-dimensional imaging devices are respectively one-dimensional CCD cameras.

3. An apparatus for detecting cut-edge flaws in transparent plates set fourth in claim 2 wherein:
said first and second linear light source are respectively disposed at a 45 degree angle to the travelling direction of glass plate.

4. An apparatus for detecting cut-edge flaws in transparent plates comprising:
a first linear light source disposed on any one side of a travelling glass plate, in parallel with glass plate and obliquely with respect to the travelling direction of glass plate;

a first one-dimensional imaging device disposed on the other side of glass plate and the arranging direction of whose imaging elements is parallel with the first linear light source for detecting light emitted from the first linear light source and transmitted through glass plate;

a first discriminator for judging the acceptability of glass plate based on the out put from the first one-dimensional imaging device;

a second linear light source disposed on any one side of glass plate, in parallel with glass plate and obliquely with respect to the travelling direction of glass plate;

a second one-dimensional imaging device disposed on the same side of glass plate as the second linear light source and the arranging direction of whose imaging elements is parallel with the second linear light source for detecting light emitted from the second linear light source and reflected by the surface of glass plate; and a second discriminator for judging the acceptability of glass plate based on the output from the second one-dimensional imaging device.

5. An apparatus for detecting cut-edge flaws in glass plates set forth in claim 4 wherein:
the first and second linear light sources are respectively fluorescent lamp; and
the first and second one-dimensional imaging devices are respectively one-dimensional CCD camera.

6. An apparatus for detecting cut-edge flaws in glass plates set fourth in claim 5 wherein:
the first and second discriminators, respectively, judge the acceptability of glass plate by processing the output waveform from the corresponding CCD camera, discriminating the size of the flaw and comparing the flaw size with reference values.

7. An apparatus for detecting cut-edge flaws in transparent plates set forth in claim 6 wherein:
the second discriminator means also calculates coordinate data by assuming bit change points of the output waveform from the corresponding CCD camera as corners of the transparent plate, calculates imaginary straight-lines connecting said corners of the transparent plate, determines a difference between coordinate data and said imaginary straight-lines, and calculates size of the flaws from said difference.

8. An apparatus for detecting cut-edge flaws in transparent plates set forth in claim 7 wherein:
the size of flaw is evaluated by two parameters of "length L" parallel with the side of glass plate and "width D" perpendicular to the side of glass plate.

9. An apparatus for detecting cut-edge flaws in transparent plates set forth in claim 8 wherein:
the "length L" and the "width D" of the flaw are compared with the reference values stored in advance in the first and second discriminators to judge the acceptability of glass plate.

10. An apparatus as set forth in claim 9 wherein:
the apparatus detects chips, serrations and other flaws which were formed by gouging glass plate in the through-thickness direction, and detects burrs, notches and other flaws which were protruded or notched from the cut lines of glass plate.

11. An apparatus for detecting cut-edge flaws in glass plates set forth in claim 4 wherein:
the first and second linear light sources are respectively disposed at a 45 degree angle to the travelling direction of glass plate.

12. An apparatus for detecting flaws in transparent plates, comprising:
a light source disposed on a first side of the plate;
a first imaging means disposed on said first side of the plate for scanning light emitted from said light source and reflected by segments along a line on the plate, and for transmitting a first signal having bits representative of said reflected light in corresponding segments;
movement means for relative movement between the plate, and said light source and said first imaging means, causing said first imaging means to completely and obliquely scan the plate;
a first discriminator means for receiving said first signal from said first imaging means and identifying flaws, corners and sides of the plate.

13. An apparatus in accordance with claim 10, wherein:

said discriminator means identifies corners by bit change points in said first signal.

14. An apparatus in accordance with claim 10, wherein:
said discriminator means identifies sides by calculating imaginary straight lines connecting said corners.

15. An apparatus in accordance with claim 12, wherein:
said discriminating means identifies flaws by measuring light changes removed from said imaginary line.

16. An apparatus in accordance with claim 10, further comprising:
a second imaging means, substantially parallel to said first imaging means, disposed on a second side of the plate for scanning segments of light transmitted along a line through the plate from said light source, and transmitting a second signal representative of said transmitted light segments;
said discriminator means also receiving said second signal and identifying through-thickness direction flaws in the plate.

17. An apparatus in accordance with claim 16, wherein:
said discriminator means identifies a location of the through-thickness flaws with respect to said identified corners and sides of the plate.

* * * * *

UNITED STATES PATENT AND TRADEMARK OFFICE
CERTIFICATE OF CORRECTION

PATENT NO. : 5,311,276
DATED : May 10, 1994
INVENTOR(S) : Igisu et al.

It is certified that error appears in the above-identified patent and that said Letters Patent is hereby corrected as shown below:

On the title page, Items
[19] Igisu et al.

[75] Inventors: Masao Igisu

Signed and Sealed this

Sixth Day of September, 1994

Attest:

BRUCE LEHMAN

*Attesting Officer*  *Commissioner of Patents and Trademarks*